United States Patent [19]

Christensen et al.

[11] Patent Number: 5,688,786
[45] Date of Patent: Nov. 18, 1997

US005688786A

[54] β-LACTAM ANTIBIOTICS

[75] Inventors: Burton Christensen, Lebanon, N.J.; Tomasz Glinka, Sunnyvale, Calif.; Ving J. Lee, Los Altos, Calif.; Scott Hecker, Los Gatos, Calif.

[73] Assignee: Microcide Pharmaceuticals, Inc., Mountain View, Calif.

[21] Appl. No.: 457,673

[22] Filed: Jun. 1, 1995

Related U.S. Application Data

[63] Continuation-in-part of Ser. No. 413,712, Mar. 30, 1995, Pat. No. 5,604,218, Ser. No. 413,713, Mar. 29, 1995, Ser. No. 413,714, Mar. 29, 1995, Pat. No. 5,607,926, Ser. No. 415,064, Mar. 29, 1995, Ser. No. 415,065, Mar. 29, 1995, abandoned, Ser. No. 415,069, Mar. 29, 1995, Pat. No. 5,593,986, and Ser. No. 455,969, May 31, 1995, which is a continuation-in-part of Ser. No. 415,065, which is a continuation-in-part of Ser. No. 222,262, Apr. 1, 1994, said Ser. No. 413,712, said Ser. No. 413,713, said Ser. No. 413,714, said Ser. No. 415,064, said Ser. No. 415,065, said Ser. No. 415,069, each is a continuation-in-part of Ser. No.369,798, Jan. 6, 1995, abandoned, which is a continuation-in-part of Ser. No. 222,262, Apr. 1, 1994, abandoned.

[51] Int. Cl.[6] .................... C07D 463/13; C07D 505/12; A61K 31/44
[52] U.S. Cl. ...................... 514/210; 540/301; 540/205
[58] Field of Search .......................... 540/301, 205; 514/210

[56] References Cited

U.S. PATENT DOCUMENTS

| | | | |
|---|---|---|---|
| 3,992,377 | 11/1976 | Chauvette et al. | 260/243 C |
| 4,066,641 | 1/1978 | Hamashima et al. | 544/17 |
| 4,123,528 | 10/1978 | Cama et al. | 424/248.52 |
| 4,150,156 | 4/1979 | Beattie et al. | 424/246 |
| 4,153,714 | 5/1979 | Ponsford | 424/274 |
| 4,256,739 | 3/1981 | Woodward et al. | 424/200 |
| 4,497,811 | 2/1985 | Shibahara et al. | 514/231 |
| 4,782,145 | 11/1988 | Brighty et al. | 540/214 |
| 4,870,168 | 9/1989 | Baker et al. | 540/222 |
| 4,992,542 | 2/1991 | Christensen et al. | 540/350 |
| 5,025,006 | 6/1991 | Dininno et al. | 514/210 |
| 5,077,287 | 12/1991 | Temansky | 540/226 |
| 5,138,048 | 8/1992 | Tamburini et al. | 540/200 |
| 5,162,521 | 11/1992 | Farina et al. | 540/226 |
| 5,196,528 | 3/1993 | Perboni et al. | 540/200 |
| 5,205,006 | 4/1993 | Panasuk | 7/108 |

FOREIGN PATENT DOCUMENTS

| | | |
|---|---|---|
| 0002210 | 6/1979 | European Pat. Off. . |
| 0009008 | 3/1980 | European Pat. Off. . |
| 0010317 | 4/1980 | European Pat. Off. . |
| 0011173 | 5/1980 | European Pat. Off. . |
| 0074599 | 3/1983 | European Pat. Off. . |
| 0090366 | 10/1983 | European Pat. Off. . |
| 0113101 | 7/1984 | European Pat. Off. . |
| 0154253 | 9/1985 | European Pat. Off. . |
| 0160391 | 11/1985 | European Pat. Off. . |
| 0182301 | 5/1986 | European Pat. Off. . |
| 0214462 | 3/1987 | European Pat. Off. . |
| 0238285 | 9/1987 | European Pat. Off. . |
| 0243686 | 11/1987 | European Pat. Off. . |
| 0010312 | 4/1990 | European Pat. Off. . |
| 0405217 | 2/1991 | European Pat. Off. . |
| 0416953 | 3/1991 | European Pat. Off. . |
| 0422596 | 4/1991 | European Pat. Off. . |
| 0502465 | 9/1992 | European Pat. Off. . |
| 0502468 | 9/1992 | European Pat. Off. . |
| 0504404 | 9/1992 | European Pat. Off. . |
| 0507313 | 10/1992 | European Pat. Off. . |
| 0517065 | 12/1992 | European Pat. Off. . |
| 0527686 | 2/1993 | European Pat. Off. . |
| 0560365 | 9/1993 | European Pat. Off. . |
| 0574940 | 12/1993 | European Pat. Off. . |
| 2282895 | 3/1976 | France . |
| 2293935 | 7/1976 | France . |
| 60-105682 | 6/1985 | Japan . |
| 61-33190 | 2/1986 | Japan . |
| 61-63684 | 4/1986 | Japan . |
| 4261182 | 9/1992 | Japan . |
| 733777 | 3/1995 | Japan . |
| 0605998 | 8/1974 | Switzerland . |
| 0605999 | 8/1974 | Switzerland . |
| 644382 | 7/1984 | Switzerland . |
| 9109037 | 6/1991 | WIPO . |
| 9507283 | 3/1995 | WIPO . |

OTHER PUBLICATIONS

Meiji Seika Kiasha *Chemical Abstract* 103:215073, searched by CAS Online (1985).

Meiji Seika Kaisha *Derwent World Patents Index*, Abstract No. 85–175578, JP 60105682 (1985).

Aszodi et al., "Synthesis and Antibacterial Activity of Isocephems," *Recent Advances in the Chemistry of β–Lactam Antibiotics*, Special Publication No. 70, pp. 350–364, Cambridge, England, Jul. 3–6 (1988).

Afonso et al., "New Synthesis of Penems, the Oxalimide Cyclization Reaction," *J. Amer. Chem. Soc.* 104:6138–6139 (1982).

Baldwin and Cooper, "Direct 6–Methoxylation of Penicillin Derivatives. A Convenient Pathway to Substituted β–Lacatam Antibiotics," *J. Amer. Chem. Soc.* 95:2401–2404 (1973).

Barrett, A.G.M., "Amide Transacylation in Penicillin and Cephalosporin Derivatives," *J.C.S. Perkin I* pp. 1629–1633 (1979).

Basker et al., "Synthesis and Antibacterial Activity of C–2 Carboxyethenylthio–Carbapenem Derivatives," *J. Antibiotics* XLIII:847–857 (1990).

(List continued on next page.)

*Primary Examiner*—Matthew V. Grumbling
*Assistant Examiner*—King Lit Wong
*Attorney, Agent, or Firm*—Lyon & Lyon LLP

[57] ABSTRACT

The present invention includes novel compounds or their pharmacologically acceptable salts which exhibit antibiotic activity against a wide spectrum of organisms including organisms which are resistant to β-lactam antibiotics and are useful as antibacterial agents. The invention also relates to novel intermediates useful for making the novel compounds of the present invention and to novel methods for producing the novel compounds and intermediate compounds.

22 Claims, No Drawings

OTHER PUBLICATIONS

Bateson et al., "Synthesis of 7-Oxo-3-sulphinyl-1-azabicyclo[3.2.0]hept-2-ene-2-carboxylates: Olivanic Acid Analogues," *J.C.S. Chem. Comm.* 185-186 (1980).

Chauvette, "Chemistry of Cephalosporin Antibiotics. XXI. Conversion of Penicillin to Cephalexin," *J. Org. Chem.* 36:1259-1267 (1971).

Chen et al., "Study of Preparative Separation of Cephalosporins By Centrifugal TLC," *Kangshengsu* 14;161-167 (1989).

Doyle et al., "Nuclear analogs of β-lactam antibiotics. XIII. Structure activity relationships in the isocephalosporin series," *Can. J. Chem.* 58:2508-2523 (1980).

Duan et al., "Solvent Optimization of Reversed Phase High Performance Liquid Chromatographic Separation by Orthogonal Design," *Zhongguo Yaoke Daxue Xuebao* 18:126-129 (1987).

Ernest et al., "119. 2-Oxocephems and 2-Acetylpenems—Selective Formation in an Intramolecular Witting Reaction," *Helvetica Chimica Acta* 64:1303-1311 (1981).

Farina et al., "A General Route to 3'Functionalized 3-Norcephalosporins," *J. Org. Chem.* 54:4962-4966 (1989).

Fetter and Lempert, "Simple and Condensed β-Lacatams. Part 8—The Preparation and Reactions of Some 4-Oxo-azetidin-2-ylacetic Acid Derivatives, and a Synthesis of p-Nitrobenzyl (5RS, 6SR)-2-(2-Formylamino-ethylthio)-6-(2-methyl-1, 3-dioxolan-2-yl) carbapen-2-em-3-carboxylate, a Compound Related to the Antibiotic Thienamycin," *J. Chem. Research*, pp. 0349-0367 (1987).

Firestone and Christensen, "Functionalization of Penicillins at Carbon 6 via N-Acylimines. 6-Hydroxypenicillin. Substituted Penicillins and Cephalosporins. VIII," *J. Org. Chem.* 38:1436-1437 (1973).

Hamashima et al., "Synthetic Studies on β-Lacatam Antibiotics. 19. Synthesis of 3-Nor-Type 1-Oxacephems," *Tetrahedron Lett.* 51:4947-4950 (1979).

Hatanaka and Ishimaru, "A Simple Synthesis of (±)-1-Carbacephem Derivatives," *Tetrahedron Lett.* 24:4837-4838 (1983).

Kamachi et al., "Direct Introduction of a Formamido Group into the 7α(6α)-Position of Cephalosporins (Penicillins), " *J. Antibiotics* pp. 820-829 (1990).

Kang, H.Y., "Synthesis and Biological Evaluation of New Aminothiazolyl Cephalosporins with Elongated Side Chains," *Bull. Korean Chem. Soc.* 12:666-673 (1991).

Kondo et al., "New 2"-Amino Derivatives of Arbekacin, Potent Aminoglycoside Antibiotics Against Methicillin-Resistant," *J. Antibiotics* 46:531-534 (1993)

Kopppel and Koehler, "Functionalization of $C_{6(7)}$ of Penicillins and Cephalosporins. A One-Step Stereoselective Synthesis of 7-α-Methoxycephalosporin C," *J. Amer. Chem. Soc.* 95:2403-2404 (1973).

Lunn and Mason, "The Synthesis of 7α-Methoxy-7β-Amidocephalosporanic Acids by Methoxylation of 7β-(p-Nitrobenzyloxycarboxamido) Cephalosporanic Acid," *Tetrahedron Lett.* 14:1311-1313 (1974).

McCombie et al., "Synthesis of 3-Heterosubstituted Isocephem and Iso-Oxacephem Antibiotics," *Tetrahedron Lett.* 27:305-308 (1986).

Melillo et al., "A Practical Synthesis of (±)-Thienamycin," *Tetrahedron Lett.* 21:2783-2786 (1980).

Mochida et al., "Synthesis and Antibacterial Activity of Novel 3-Substituted Carbacephems," *J. Antibiotics* vol. XLII pp. 283-292 (1989).

NCCLS publication entitled Methods for Dilution Antimicrobial Susceptibility Tests for Bacterial That Grow Aerobically—Third Edition; Approved Standard, NCCLS 13(25) (1993).

Oh and Cho, "Studies on the Synthesis and Antibacterial Activity of New Zwitterionic Carbapenems," *J. Antibiotics* 47:126-128 (1994).

Ohki et al., "FK037. A New Parenteral Cephalosporin With a Boraid Antibacterial Spectrum: Synthesis and Antibacterial Activity," *J. Antibiotics* 46:359-361 (1993).

Oida et al., "2-(Alkylthio)penem-3-carboxylic Acids. I. Synthesis of 6-Unsubstituted Penems)," *Chem. Pharm. Bull.* 28:3232-3243 (1980).

Perboni et al., "Ch. 2—Tribactams: A Novel Class of β-Lactam Antibiotics," in *Recent Advances in the Chemistry of Anti-Infective Agents*, pp. 21-35, Bentley and Ponsford, eds, Royal Society of Chemistry (1993).

Phillips and O'Neill, "A Convergent Process to C-2 Substituted Penems via Addition of Thiois and Organocuprates to an O-Triflylthloketene Acetal," *Tetrahedron Lett.* 23:3291-3294 (1990).

Ponsford and Southgate, "Preparation of 8-Oxo-7-(1-hydroxyethyl)-3-oxa-1-azabicyclo[4.2.0]octane Derivatives: Intermediates for Thienamycin Synthesis," *J.C.S. Chem. Comm.* 19:846-847 (1979).

Sanders et al., "Microbiological Characterization of Everninomicins B and D," *Antimicro. Agents Chemother.* 6:232-238 (1974).

Shih et al., "Synthetic Carbapenem Antibiotics 1. 1-β-Methylcarbapenem," *Heterocycles* 21:29-40 (1984).

Shibata and Sugtimura, "Synthetic Studies of 1-β-Methylcarbapenem Antibiotics," *J. Antibiotics* 42:374-381 (1989).

Spangler et al., "Susceptibilities of Penicillin-Susceptible and -Resistant Strains of *Streptococcus pneumoniae* RP 59500, Vancomycin, Erythromycin, PD 131628, Sparfloxacin, Temafloxacin, Win 57273, Ofloxacin, and Ciprofloxacin," *Antimicro. Agents Chemother.* 36:856-859 (1992).

Sum et al., "Glycylcyclines. 1. A New Generation of Potent Antibacterial Agents through Modification of 9-Aminotetracyclines," *J. Med. Chem.* 37:184-188 (1994).

Sunagawa et al., "Synthesis and Biological Properties of 1β-Methyl-Carbapenems with N-Methylpyrrolidinylthio Group at C-2 Position," *J. Antibiotics* 45:971-976 (1992).

Sunagawa et al., "New Penem Compounds with 5'-Substituted Pyrrolidinylthio Group as a C-2 Side Chain; Comparison of their Biological Properties with Those of Carbapenem Compounds," *J. Antibiotics* 45:500-504 (1992).

Ternansky et al., "Discovery and Structure-Activity Relationship of a Series of 1-Carba-1-dethiacephems Exhibiting Activity against Methicillin-Resistant *Staphylococcus aureus*," *J. Med. Chem.* 36:1971-1976 (1971).

Tsubouchi et al., "A Convenient One Pot Asymmetric Synthesis of cis-β-Lactams: Key Precursors for Optically Active 2-Oxaisocephems," *Tetrahedron: Assymetry* 5:441-452 (1994).

Tsuchiya, "Cefsulodin (SCE-129), Cefotiam (SCE-963), and Cefmenoxime (SCE-1365)," *Beta-Lactam Antibiot.* pp. 107-119 (1981).

Yokoo et al., "Studies on Cephalosporin Antibiotics," *J. Antibiotics* 44:498–506 (1991).

Yoshida et al., "An Efficient Carbapenem Synthesis via an Intramolecular Witting Reaction of New Trialkoxphosphorane–Thiolesters," *Tetrahedron Lett.* 25:2793–2796 (1984).

Yoshida et al., "New Synthesis of Penems via Reductive Cyclization Reaction of Oxalimides with Trialkyl Phosphite," *Chem. Pharm. Bull.* 31:768–771 (1983).

Yoshioka et al., "Stereocontrolled, Straightforward Synthesis of 3–Subsituted Methyl 7α–Methoxy–1–Oxacephems," *Tetrahedron Lett.* 21:351–354 (1980).

β-LACTAM ANTIBIOTICS

BACKGROUND OF THE INVENTION

1. Related Applications

The present application is a continuation-in-part of U.S. applications Ser. Nos. 08/413,712 (now U.S. Pat. No. 5,604,218, filed Mar. 30, 1995), 08/413,713, 08/413,714 (now U.S. Pat. No. 5,607,926), 08/415,064, 08/415,065 (now abandoned), and 08/415,069 (now U.S. Pat. No. 5,593,986), all filed Mar. 29, 1995 and all of which are continuation-in-part applications of Ser. No. 08/369,798, filed Jan. 6, 1995 (now abandoned) which is a continuation-in-part application of U.S. application, Ser. No. 08/222,262, filed Apr. 1, 1994 (now abandoned), all of which are incorporated herein by reference in their entirety, including any drawings.

The present application is also a continuation-in-part of U.S. patent application entitled "Cephalosporin Antibiotics", filed May 31, 1995, U.S. Ser. No. 08/455,969 to be assigned, which is a continuation-in-part of U.S. application Ser. No. 08/415,065, filed Mar. 29, 1995, which is a continuation-in-part of Ser. No. 08/222,262, filed Apr. 1, 1994, all of which are incorporated herein by reference in its entirety, including any drawings.

2. Field of the Invention

The present invention relates to β-lactam antibiotics. More particularly, the present invention includes novel β-lactam compounds and their pharmacologically acceptable salts and prodrugs, their methods of production and use. These compounds exhibit antibiotic activity against a wide spectrum of organisms, including organisms which are resistant to β-lactam antibiotics.

3. Review of the Background Art

Over the past three decades a large variety of antibiotics has become available for clinical use. One class of antibiotics which has seen remarkable growth are the β-lactams, over 70 of which have entered clinical use for the treatment of bacterial infections in mammals since 1965.

The β-lactams exhibit their antibacterial activity by inhibiting bacterial peptidoglycan biosynthesis, and have been extremely effective in treating a wide variety of bacterial infections. β-lactams that are said to have antibacterial activity are described in U.S. Pat. No. 3,992,377 and U.S. Pat. No. 4,256,739.

Unfortunately, the wide-spread and indiscriminant use of these antibiotics has led to a rapid increase in the number of bacterial strains which are resistant to these compounds. Most importantly, this resistance has emerged among clinically important microorganisms which threaten to limit the utility of presently available β-lactam antibiotics. In particular, resistant strains of Salmonella, *S. pneumoniae*, Enterobacteriaceae, and Pseudomonas have emerged which threaten to undo many of the strides made in reducing mortality and morbidity from bacterial infections.

Bacterial resistance to β-lactams follows three major pathways: a) the development of β-lactamases capable of inactivating the β-lactam ring; b) decreased β-lactam penetration into the bacteria due to changes in bacterial cell wall composition; and c) poor binding to penicillin-binding proteins (PBPs). The latter pathway is especially important, as the binding of β-lactams to PBPs is essential for inhibiting bacterial cell-wall biosynthesis. Certain Gram-positive bacteria, namely methicillin-resistant *Staphylococcus aureus* ("MRSA") and enterococci are highly resistant to β-lactam antibiotics. Resistance in MRSA is due to the presence of high levels of an unusual PBP, PBP2a, which is insensitive, or binds poorly, to β-lactam antibiotics. The activity of β-lactam antibiotics against PBP2a-containing organisms has been shown to correlate well with the binding affinity of the antibiotic to PBP2a. Currently, the glycopeptides vancomycin and teicoplanin are primarily used for MRSA bacteremia. The quinolone antibacterials and some carbapenems, such as imipenem, have been reported to be active against a few MRSA strains, but their use is restricted due to emerging resistant MRSA strains.

Experimental compounds which may possess utility as anti-MRSA or anti-enterococcal bactericides include the glycylcyclines (see, e.g., P.-E. Sum et al., *J. Med. Chem.*, 37, (1994)), FK-037 (see, e.g., H. Ohki et al., *J. Antibiotics*, 46:359–361 (1993)), RP-59,500 (see, e.g., S. K. Spangler et al., *Antimicro. Agents Chemother.*, 36:856–9 (1992)), the everninomycin complex (see, e.g., W. E. Sanders et al., *Antimicro. Agents Chemother.*, 6: 232–8 (1974)), the 2-(biaryl)carbapenems (see, e.g., U.S. Pat. No. 5,025,006), 3-(benzothiazolylthio)cephems (see, e.g., EP Application No. 527686), 3-(thiazolylthio)carbacephems (see, e.g., R. J. Ternansky et al., *J. Med. Chem.*, 36:1971 (1993) and U.S. Patent No. 5,077,287) and arbekacin (S. Kondo, et al. *J. Antibiotics* 46:531 (1993).

SUMMARY OF THE INVENTION

The present invention includes compounds, compositions and methods effective to treat infections in mammals arising from β-lactam antibiotic resistant bacteria.

In one aspect the present invention features compounds that have antibiotic activity against an organism resistant to a β-lactam antibiotic. In vitro and in vivo data showing the effectiveness of these compounds is provided in U.S. applications Ser. Nos. 08/413,712, 08/413,713, 08/413,714, 08/415,064, 08/413,065, and 08/413,069, filed Mar. 29, 1995 and U.S. Ser. No. unassigned, filed May 15, 1995, entitled "Cephalosporin Antibiotics". That data demonstrated potent activity for certain pharmacophores appended to selected β-lactam nuclei. In particular, compounds having thio-linked aryl pharmacophores as illustrated in the compounds of Structures II, III, IV and V below were shown to have good effect:

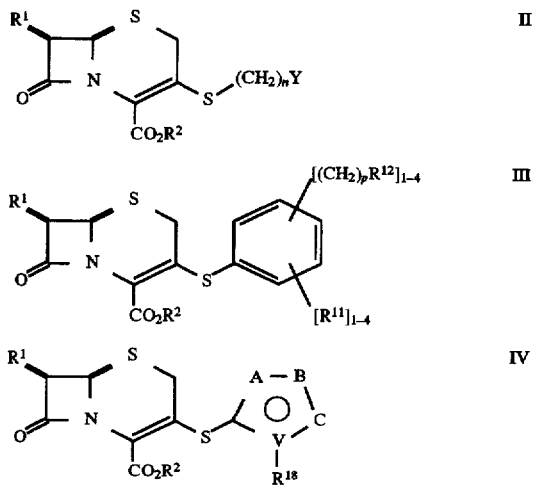

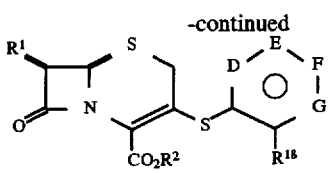
V

In another aspect, other β-lactam antibiotic compounds encompassed by the present invention are compounds having the thio linked aryl and heteroaryl pharmacophores shown above appended to other β-lactam nuclei as described in detail herein. Examples of several classes of such compounds are provided herein and techniques are presented for making such compounds and using them both in vitro and in vivo. Such compounds preferably have a minimum inhibitory concentration (MIC) that is less that 50%, more preferably less than 10%, and most preferably less than 1% of the MIC of the Cefotaxime for a β-lactam resistant organism, such as those previously listed in Table 1 of of U.S. applications Ser. Nos. 08/413,712, 08/413,713, 08/413,714, 08/415,064, 08/413,065, and 08/413,069, filed Mar. 29, 1995, preferably a β-lactam resistant Staphylococcal or Enterococcal organism. Other preferred compounds are able to prevent or reduce mortality in mice infected with the β-lactam resistant organism to a greater extent that vancomycin or cefotaxime.

In one embodiment, the present invention includes a compound of the formula selected from the group consisting of:

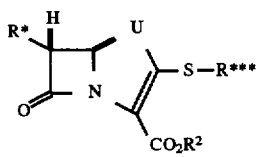 A

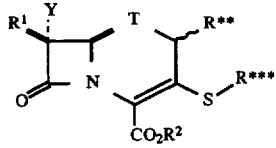 B

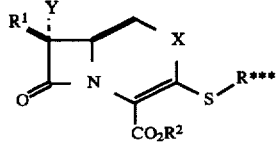 C and

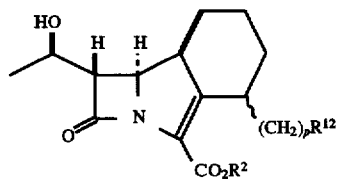 D and its pharmaceutically acceptable salts and prodrugs, wherein:

X is selected from the group consisting of $CH_2$, S, and O;
T is selected from the group consisting of $CH_2$ and O;
U is selected from the group consisting of $CH_2$, S, O, and CH(alkyl), where alkyl is $C_1$ to $C_4$;
Y is selected from the group consisting of H, OMe, and NHCHO;
R* is selected from the group consisting of $CH(OH)CH_3$, $C(OH)(CH_3)_2$, $CHFCH_3$, and $CH=CH_2$;

R** is selected from the group consisting of H, Me, or Et;
$R^1$ is selected from the group consisting of —NHC(O) $ZR^3$; —$NR^4R^5$, and

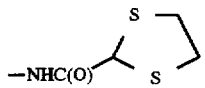

where Z is selected from the group consisting of —$CH_2$ $(X^*)_m$—, —$C(NOR^6)$—, —$CH(OR^7)$—, —$C(CHCO_2R^8)$— and —$CH(NR^9R^{10})$—, X* is selected from the group consisting of O and S,
m is 0 or 1;
$R^3$ is selected from the group consisting of cyano, alkyl, aryl, heterocycle and heteroaralkyl;
$R^{4-7}$ are independently selected from the group consisting of hydrogen, alkyl, aryl and acyl;
$R^8$ may be selected from the group of hydrogen, alkyl and aryl;
$R^9$ and $R^{10}$ are selected independently from the group consisting of hydrogen, alkyl, acyl, and heterocyclecarbonyl;
$R^2$ is selected from the group consisting of hydrogen, alkyl, alkenyl, aryl, heterocycle, aralkyl, heteroaralkyl, and trialkylsilyl;
$R^{12}$ is

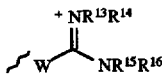

or S—$R^{17}$

W is selected from the group consisting of S, NH, and $CH_2$, except in structure A when U is $CH_2$, wherein W is selected from the group consisting of S and $CH_2$;

$R^{13}$–$R^{16}$ are independently selected from the group consisting of H, alkyl, cycloalkyl, acyl, hydroxy, amino, amidino, and phosphoryl and taken together may form a 5- or 6-membered ring;

$R^{17}$ is selected from the group consisting of alkyl, cycloalkyl, and a 5- or 6-membered ring heterocycle containing 0–4 nitrogen atoms, 0–1 oxygen atoms, and 0–1 sulfur atoms, and which is optionally substituted by alkyl, hydroxyl, alkoxyl, amino, hydroxymethyl, aminomethyl, or mono- or dialkylaminomethyl;

p is 0, 1 or 2;
R*** is selected from the group consisting of heterotricycle;

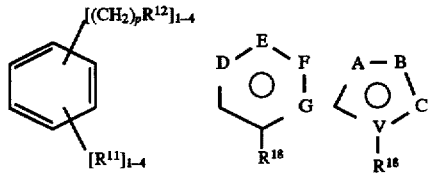

wherein $R^{11}$ is H or halogen;
$R^{18}$ is cyano or an optionally substituted phenyl or heteroaryl;
V is carbon or nitrogen;
A, B and C are independently selected from the group consisting of $CR^{19}$, nitrogen and sulphur, where $R^{19}$ is hydrogen, alkyl, hydroxyl, amino, cyano, hydroxymethyl, or mono- or dialkylaminomethyl; and D, E, F, and G are independently selected from the group consisting of $CR^{19}$ or nitrogen, where $R^{19}$ is selected from the group consisting of hydrogen, alkyl, hydroxyl, amino, cyano, hydroxymethyl, and mono- or dialkylaminomethyl.

The specific juxtaposition of groups A–C and D–G is limited to examples of heterocyclic groups known in the chemistry arts. Specific examples of these heterocyclic groups include the following:

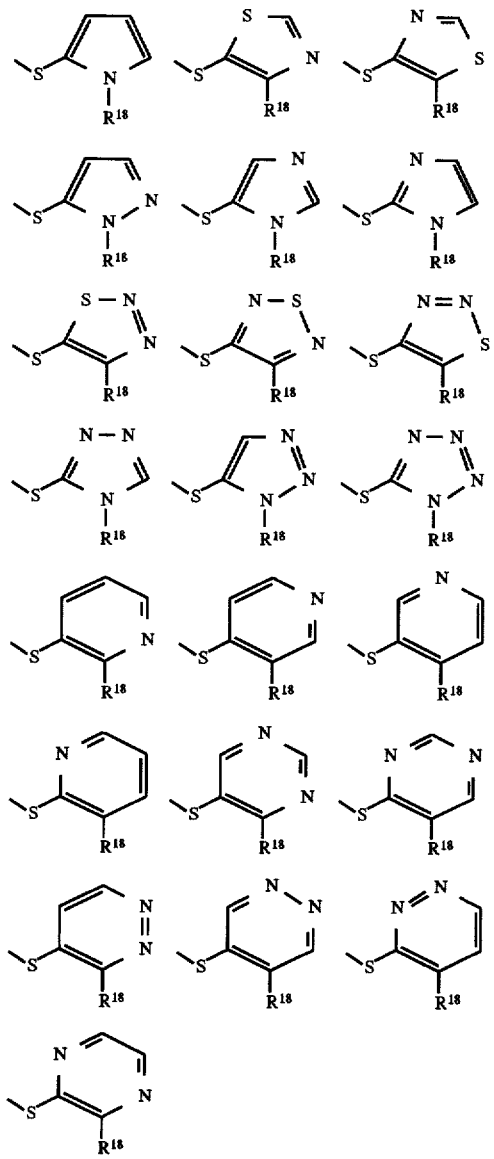

Preferred compounds include those compounds wherein the groups A–C, V and D–G are pyrazole, thiadiazole and pyridine, and $R^{18}$ is optionally-substituted phenyl, pyridyl, pyrazolyl, or cyano.

In another embodiment, the present invention provides for compositions comprising an amount of the compound of Structures A, B, C and/or D effective to treat bacterial infections in mammals arising from bacteria resistant to β-lactam antibiotics and a pharmaceutically acceptable carrier or diluent.

In still another embodiment, the present invention includes methods for treating a bacterial infection in a mammal arising from bacteria resistant to β-lactam antibiotics comprising administering to a mammal suffering from such an infection a therapeutically effective amount of a compound of Structure A, B, C and/or D.

Other features and advantages of the invention will be apparent from the following description of the preferred embodiments thereof and from the claims.

DESCRIPTION OF THE PREFERRED EMBODIMENTS

I. Definitions

As used herein, the term "alkyl" denotes branched or unbranched hydrocarbon chains containing between one and six, preferably one and four, carbon atoms, such as, e.g., methyl, ethyl, n-propyl, iso-propyl, n-butyl, sec-butyl, iso-butyl, tert-butyl, and 2-methylpentyl. These groups may be optionally substituted with one or more functional groups which are attached commonly to such chains, such as, e.g., hydroxyl, bromo, fluoro, chloro, iodo, mercapto or thio, cyano, alkylthio, heterocycle, aryl, heteroaryl, carboxyl, alkoxycarbonyl, alkyl, alkenyl, nitro, amino, alkoxyl, amido, and optionally substituted isothioureido, amidino, guanidino, and the like to form alkyl groups such as trifluoromethyl, 3-hydroxyhexyl, 2-carboxypropyl, 2-fluoroethyl, carboxymethyl, 4-cyanobutyl, 2-guanidinoethyl, 3-N,N'-dimethylisothiouroniumpropyl, and the like.

The term "alkenyl" denotes an alkyl group as defined above having at least one double bond, e.g., allyl, 3-hydroxy-2-buten-1-yl, 1-methyl-2-propen-1-yl and the like.

The term "aryl" denotes a chain of carbon atoms an which form an least one aromatic ring having preferably between about 6–14 carbon atoms, such as, e.g., phenyl, naphthyl, indenyl, and the like, and which may be substituted with one or more functional groups which are attached commonly to such chains, such as, e.g., hydroxyl, bromo, fluoro, chloro, iodo, mercapto or thio, cyano, cyanoamido, alkylthio, heterocycle, aryl, heteroaryl, carboxyl, alkoxycarbonyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, cyanophenyl, pyridylphenyl, pyrrolylphenyl, pyrazolylphenyl, triazolylphenyl, tetrazolylphenyl and the like.

The term "heterocycle" denotes a chain of carbon and at least one non-carbon atoms which together form one or more aromatic or non-aromatic rings having preferrably between about 6–14 atoms, such as, e.g., furyl, thienyl, imidazolyl, indolyl, pyridinyl, thiadiazolyl, thiazolyl, piperazinyl, dibenzfuranyl, dibenzthienyl. These rings may be optionally substituted with one or more functional groups which are attached commonly to such rings, such as, e.g., hydroxyl, bromo, fluoro, chloro, iodo, mercapto or thio, cyano, cyanoamido, alkylthio, heterocycle, aryl, heteroaryl, carboxyl, oxo, alkoxycarbonyl, alkyl, alkenyl, nitro, amino, alkoxyl, amido, and the like to form rings such as, e.g., 2-aminothiazol-4-yl, 2,3-dioxopiperazinyl, 4-alkylpiperazinyl, 2-iodo-3-dibenzfuranyl and 3-hydroxy-4-dibenzthienyl and the like.

The term "heteroaromatic" or "heteroaryl" (HetAr) denotes an aromatic heterocycle as defined above.

The term "heterotricycle" denotes an aromatic heterocyclic substituent as defined above which comprises three aromatic rings.

The term "heterocyclecarbonyl" denotes the group —C(O)Het, where Het is heterocycle as defined above.

The term "alkoxyl" denotes the group —OR, where R is alkyl as defined above, such as methoxy, ethoxy, n-propoxy, iso-propoxy, n-butoxy, sec-butoxy, iso-butoxy, tert-butoxy, trifluoromethoxy, 3-hydroxyhexyloxy, 2-carboxypropyloxy, 2-fluoroethoxy, carboxymethoxy and cyanobutyloxy and the like.

The term "alkylthio" denotes the group —SR, where R is alkyl as defined above, such as methylthio, ethylthio, n-propylthio, iso-propylthio, n-butylthio, sec-butylthio, iso-butylthio, tert-butylthio, trifluoromethylthio, 3-hydroxyhexylthio, 2-carboxypropylthio, 2-fluoroethylthio, carboxymethylthio and cyanobutylthio and the like.

The term "acyl" denotes groups —C(O)R, where R is alkyl as defined above, such as formyl, acetyl, propionyl, or butyryl.

The term "aryloxy" denotes groups —OAr, where Ar is an aryl group as defined above.

The term "aralkyl" denotes groups —RAr, where R is alkyl and Ar is aryl, both as defined above.

The term "heteroaralkyl" denotes groups —RHetAr where R is alkyl and HetAr is heteroaryl as defined above.

The term "trialkylsilyl" denotes the group RR'R"Si—, where R, R' and R" are alkyl as defined above.

The term "trialkylammonium" denotes the group [RR'R"N—]$^+$, where R, R' and R" are alkyl as defined above.

The term "amino" denotes the group NRR', where R and R' may independently be alkyl, aryl or acyl as defined above, or hydrogen.

The term "amido" denotes the group —C(O)NRR', where R and R' may independently be alkyl, aryl or acyl as defined above, or hydrogen.

The term "cyanoamido" refers to the group —NH—C≡N.

The term "β-lactam resistant bacteria" refers to bacteria against which a β-lactam antibiotic has an minimum inhibitory concentration (MIC) greater than 32 mg/ml.

The term "prodrug" refers to an agent that is converted into the parent drug in vivo. Prodrugs may be easier to administer than the parent drug in some situations. For example, the prodrug may be bioavailable by oral administration but the parent is not, or the prodrug may improve solubility to allow for intravenous administration.

II. Compounds of the Invention

The present invention provides compounds, methods and compositions effective to treat bacterial infections, and, especially, infections arising from bacteria which have developed resistance to conventional β-lactam antibiotics. More importantly, the present invention provides compounds, methods and compositions effective to treat bacterial infections arising from bacteria which have developed resistance to conventional β-lactam antibiotics.

A. Preferred Embodiments of Structures A–D

With respect to $R^3$, especially preferred embodiments are those compounds wherein $R^3$ is cyano, alkyl, aryl, heterocycle or heteroaralkyl. Other preferred embodiments include those wherein $R^3$ is hydroxyphenyl, preferably 4-hydroxyphenyl, heterocycle and heteroaralkyl. Preferred heterocycle substituents include thienyl, furyl and thiazolyl, especially 2-thienyl, 2-furyl, and optionally substituted heterocycles such as 2-aminothiazol-4-yl.

With respect to Z, preferred embodiments include those wherein Z is methylene, substituted oxyiminomethylene (—C(NOR)—), substituted oxymethylene (—CH(OR)—), substituted (carboxymethylene)methylene (—C(CHCO$_2$R)—), and aminomethylene (—CH(NRR')—). Preferred substituents for Z=oxyiminomethylene, oxymethylene and (carboxymethylene)methylene include hydrogen, alkyl, aryl and heterocycle. Such groups include, e.g., hydrogen, 2-fluoroethyl, cyclopropylmethyl, cyclopentyl, allyl, and dichloroallyl. Preferred substituents for Z=aminomethylene include alkyl, aryl, and heterocycle and acyl.

In another preferred embodiment, the present invention includes intermediates which are especially useful in the formation of the bactericides of the invention. Generally these intermediates include those embodiments of the invention wherein $R^1$ is —NRR', where R and R' are hydrogen, and acyl. Examples of such groups include, e.g., t-butyloxycarbonyl and benzyloxycarbonyl.

Finally, $R^2$ may be selected from the group hydrogen, alkyl, alkenyl, aryl, heterocycle, aralkyl, heteroaralkyl, alkoxyl, or trialkylsilyl. Generally, only those compounds with $R^2$=hydrogen are biologically active. However, the present invention also contemplates other $R^2$ substituents which are either easily hydrolyzed under biological conditions, i.e., such groups which can be cleaved easily after injection or ingestion of a compound of the invention by a mammalian subject (see, e.g., European Patent Application No. 527,686 A1 to Tsushima, et al., which is incorporated herein by reference). The present invention further contemplates substituents $R^2$ which are effective to protect the carboxyl group from unwanted reactions during synthesis of the compounds of the invention. Many such protective groups are well-known in the art (see, e.g., Green and Wuts, PROTECTIVE GROUPS IN ORGANIC SYNTHESIS (Wiley 1991), which is incorporated herein by reference). Examples of such groups include allyl, t-amyl, benzhydryl, t-butyl, t-butyldimethylsilyl, benzyl, 2-chloroallyl, 3,3-dimethylallyl, 2,4-dimethoxybenzyl, 3,4-dimethoxybenzyl, 4,4'-dimethoxytrityl, 4-methoxybenzyl, 2-methoxybenzyl, 4-methoxytrityl, methoxymethyl, 4-nitrobenzyl, 2-nitrobenzyl, phenacyl, 2,2,2-trichloroethyl, trimethylsilyl, 2-(trimethylsilyl)ethyl, and trityl as well as the trifluoroacetate, hydrochloride, hydrobromide and sulfate salts thereof.

Preferred compounds include those compounds wherein $R^{12}$ is

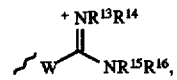

W=S, NH, or CH$_2$, p is 0, 1 or 2, and $R^{13}$–$R^{16}$ are H or lower alkyl. Especially preferred compounds include those compounds wherein $R^{12}$ is

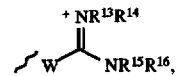

W=S, or NH, p is 1, and $R^{13}$–$R^{16}$ are hydrogen.

B. Synthesis of Compounds of Structures A–D

The compounds of the present invention may be readily prepared in accordance with the procedures described in the references provided in this section. However, it will be appreciated that other synthetic pathways for forming the compounds of the invention are available and that the following is offered merely by way of example, and not limitation. It will be further recognized that various protecting and deprotecting strategies will be employed which are standard in the art (See, e.g., Green and Wuts). Those of skill in the art will recognize that the selection of any particular protecting group (e.g., a carboxy protecting group) will depend on the stability of the protected moiety with respect to subsequent reaction conditions.

Generally, the synthesis of the β-lactams of the present invention may be achieved using well-known methods and readily available materials (see, e.g., March; Larock, COMPREHENSIVE ORGANIC TRANSFORMATIONS (VCH Publishers, 1989); and G. I. Georg, THE ORGANIC CHEMISTRY OF β-lactams, (VCH 1992), each of which is incorporated herein by reference).

The substituent $R^1$ may be any of the groups described above and are either available commercially (e.g., from Aldrich, Milwaukee, Wis.) or can be formed using known techniques and starting materials (.see, e.g., March; Larock). These groups can be substituted for those present on the starting material by variety of well known techniques (see, e.g., Barrett, J. C. S. Perkin I, 1629 (1979) or Chauvette, J. Org. Chem. 36:1259 (1971), both of which are incorporated herein by reference), such as by transamination of an existing substituent for the desired substituent, or hydrolytic removal of the existing substituent followed by reaction with a suitably reactive form of desired substituent, such as an acyl chloride. Again, the appropriate reagents and techniques will be apparent to those of skill in the art.

The carboxyl group $R^2$ may be those protecting groups amenable to reductive cleavage, such as benzyl, p- or o-nitrobenzyl, 2,2,2-trichloroethyl, allyl, cinnamyl, benzhydryl, 2-chloroallyl and the like. Alternatively, $R^2$ may be a protecting group amenable to acidic cleavage, such as t-butyl, t-amyl, trityl, 4-methoxytrityl, 4,4'-dimethoxytrityl, trimethylsilyl, t-butyldimethylsilyl, phenacyl, β-(trimethylsilyl)ethyl, benzyl, 4-(or 2-methoxybenzyl, 2,4-dimethoxybenzyl, 3,4-dimethoxybenzyl, 2,4,6-trimethoxybenzyl, methoxymethyl, benzhydryl, or 3,3-dimethylallyl. Preferred protecting groups are p-methoxybenzyl, p-nitrobenzyl, allyl and benzhydryl. Such groups may be attached to the unprotected carboxyl group of the β-lactam starting material using known reagents and techniques, such as those described in Green and Wuts.

Preferred amine protecting groups include trityl, formyl, phenoxyacetyl, trichloroacetyl, chloroacetyl, bromoacetyl, iodoacetyl, urethane-type protecting groups [such as t-butoxycarbonyl, benzyloxycarbonyl, 4-methoxybenzyloxycarbonyl, 4-nitrobenzyloxycarbonyl, 2-chloroallylcarbonyl, allyoxycarbonyl, 2-(trimethylsilyl) ethoxycarbonyl, 2,2,2-trichloroethoxycarbonyl, $(C_4-C_6)$-cycloalkanyloxycarbonyl or 9-fluorenylmethoxycarbonyl (FMOC)]. Especially preferred protecting groups are trityl, allyoxycarbonyl, benzyloxycarbonyl, phenoxyacetyl, and t-butoxycarbonyl. These may be attached and removed using standard techniques (see Green and Wuts). The selection of the amine-protecting group to be employed will depend on the stability of the protected β-lactam to the subsequent reaction conditions.

Examples of references providing methods that can be used to make compounds encompassed by the present invention are listed below and are incorporated herein by reference in their entirety, including any drawings:

1. 6-hydroxyethyl-2-[aryl(or alkyl)thio]carbapenems (Structure A, X=$CH_2$)

These compounds may be synthesized using the techniques described in: (1) D. G. Melillo, I. Shinkai, T. Liu, K. Ryan and M. Sletzinger, Tetrahedron Letters, 2783 (1980); (2) R. I. Ponsford and R. Southgate, J. C. S., Chem. Commun., 846 (1979); (3) D.H. Shih, F. Baker, L. Cama and B. G. Christensen, Heterocycles, 21, 29 (1984); (4) J. H. Bateson, P. M. Roberts, T. C. Smale and R. Southgate, J. C. S., Chem. Commun., 185 (1980); (5) European Patent Application 10,312; (6) U.S. Pat. No. 4,153,714; (7) C. -H. Oh and J. -H. Cho, J. Antibiotics, 47, 126 (1994); (8) M. Sunagawa, H. Matsumura, T. Inoue, H. Yamaga and M. Fukasawa, J. Antibiotics, 45, 971 (1992); (9) M. J. Basker, D. F. Corbett, S. Coulton and R. Southgate, J. Antibiotics, 43, 847 (1990); (10) A. Yoshida, Y. Tajima, N. Takeda and S. Oida, Tetrahedron Letters, 25, 2793 (1984); (11) J. Fetter, K. Lempert, M. Kajtar-Peredy, G. Bujtas, and G. Simig, J. Chem. Res. (S), 28 (1987); J. Chem. Res. (M), 349 (1987); and (12) T. Shibata and Y. Sugimura, J. Antibiotics, 42, 374 (1989).

2. 6-hydroxyethyl-2-[aryl(or alkyl)thio]penems (Structure A, X=S)

These compounds may be synthesized using the techniques described in (1) S. Oida, A. Yoshida, T. Hayashi, N. Takeda and E. Ohki, Chem. Pharm. Bull., 28, 3232 (1980); (2) I. Ernest, A. J. Main and R. B. Woodward, Helv. Chim. Acta., 64, 1303 (1981); (3) A. Alfonso, F. Hon, J. Weinstein and A. K. Ganguly, J. Am. Chem. Soc., 104, 6138 (1982); (4) A. Yoshida, T. Hayashi, N. Takeda, S. Oida and E. Ohki, Chem. Pharm. Bull., 31, 768 (1983); (5) U.S. Pat. Nos. 4,782,145 and 4,782,146; (6) M. Sunagawa, H. Matsumura, T. Inoue and M. Fukasawa, J. Antibiotics, 45, 500 (1992); and (7) D. Phillips and B. T. O'Neill, Tetrahedron Letters, 31, 3291 (1990).

3. 7-acylamido-3-[aryl(or alkyl)thio]carbacephems (Structure B, X=$CH_2$)

These compounds may be synthesized using the techniques described in (1) R. J. Ternansky, S. E. Draheim, A. J. Pike, F. W. Bell, S. J. West, C. L. Jordan, C. Y. Ernie Wu, D. A. Preston, W. Alborn, Jr., J. S. Kasher and B. L. Hawkins, J. Med. Chem., 36, 1971 (1993); and (2) M. Hatanaka and T. Ishimaru, Tetrahedron Letters, 24, 4837 (1983).

4. 7-acylamido-3-[aryl(or alkyl)thio]oxacephems (Structure B, X=O)

These compounds may be synthesized using the techniques described in (1) Y. Hamashima, S. Yamamoto, T. Kubota, K. Tokura, K. Ishikura, K. Minami, F. Matsubara, M. Yamaguchi, I. Kikkawa, and W. Nagata, Tetrahedron Letters, 4947 (1979).

5. 7-acylamido-3-(alkylthio)isocephems (Structure C, X=S)

These compounds may be synthesized using the techniques described in (1) J. Aszodi, A. Bonnet, J. -F. Chantot, G. Costerousse and G. Teutsch in "Recent Advances in the Chemistry of β-Lactam Antibiotics", ed. P. H. Bentley and R. Southgate, Specialist Publication No. 70, Royal Society Chemistry; London (1989)-Chapter 23; and (2) H. Tsubouchi, K. Tsuji, K. Yasumura, N. Tada, S. Nishitani, J. Minamikawa and H. Ishikawa, Tetrahedron:Asymmetry, 5, 441 (1994).

6. 3-(alkylthio)isoxacephems (Structure C, X=O)

These compounds may be synthesized using the techniques described in S. W. McCombie, W. A. Metz and A. Alfonso, Tetrahedron Letters, 27,305 (1986).

7. 7-acylamido3-(substituted)methyl related compounds

The following are examples of 7-acylamido-3-(substituted)methyl related compounds: 7-acylamido-7α-methoxy-3-[aryl(alkyl)thio]cephems (Structure B, X=S); 7-acylamido-7α-methoxy-3-[aryl(alkyl)thio]carbacephems (Structure B, X=CH$_2$); 7-acylamido-7α-methoxy-3-[aryl(alkyl)thio]oxacephems (Structure B, X=O); 7-acylamido-7α-formamido-3-[aryl(alkyl)thio]cephems (Structure B, X=S); 7-acylamido-7α-formamido-3-[aryl(alkyl)thio]carbacephems (Structure B, X=CH$_2$); and 7-acylamido-7α-formamido-3-[aryl(alkyl)thio]oxacephem (Structure B, X=O).

These classes of structures could be prepared from the 7-H precursor with precedented chemistry from the corresponding 7-acylamido-3-(substituted)methyl related nuclei using the techniques described in: (1) H. Kamachi, T. Okita, T. Yamasaki and T. Naito, J. Antibiotics, 43, 820 (1990); (2) M. Yoshioka, T. Tsuji, S. Uyeo, S. Yamamoto, T. Aoki, Y. Nishitani, S. Mori, H. Satoh, Y. Hamada, H. Ishitobi and W. Nagata, Tetrahedron Letters, 351 (1980); (3) J. E. Baldwin, F. J. Urban, R. D. G. Cooper and F. L. Jose, J. Amer. Chem. Soc., 95, 2401 (1973); (4) G. A. Koppel and R. E. Koehler, J. Amer. Chem. Soc., 95, 2403 (1973); (5) R. A. Firestone and B. G. Christensen, J. Org. Chem., 38, 1436 (1973); (6) W. H. W. Lunn and E. V. Mason, Tetrahedron Letters, 1311 (1974).

The synthesis of the following structures can be crafted by previous art described above: 7-acylamido-7α-methoxy-3-[aryl(alkyl)thio]isocephem (Structure C, X=S); 7-acylamido-7α-methoxy-3-[aryl(alkyl)thio]isoxacephem (Structure C, X=O); 7-acylamido-7α-formamido-3-[aryl(alkyl)thio]isocephem (Structure C, X=S); and 7-acylamido-7α-formamido-3-[aryl(alkyl)thio]isoxacephem (Structure C, X=O).

8. Tribactams

Various preparations of tribactam systems (Structure D) are described in the following references: (1) U.S. Pat. No. 5,196,528 (Mar. 23, 1993) Perboni et al (Glaxo Spa); (2) U.S. Pat. No. 5,138,048 (Aug. 11, 1992) Tamburine et al (Glaxo Spa); (3) EP 517,065 (Sep. 12, 1992) Hoechst AG; (4) EP Application 422,596 (Priority date=Nov. 10, 1989) Takeda; (5) EP Application 507,313 (Priority date=May 4, 1991) Takeda; (6) EP Application 416,953 Tamburine et al (Glaxo Spa); (7) "Tribactams: A Novel Class of β-lactam Antibiotics" by A. Perboni et al (p. 21–35) in *Recent Advances in the Chemistry of Anti-Infective Agents*, P. H. Bentley and R. Ponsford, ed., 1993.

III. Pharmaceutical Applications and Preparations

According to this invention, a therapeutically or pharmaceutically effective amount of a β-lactam and particularly, a compound of Structures A–D, is administered to a mammal suffering from an β-lactam resistant bacterial infection, especially resistant *S. aureus*, in an amount effective to at least partially relieve the infection. Especially important are infections resulting from β-lactam resistant strains having similar β-lactam resistant activity to strains such as *S. aureus* ATCC 29213, *S. aureus* ATCC 25913, *S. aureus* ATCC 31432, *S. aureus* col (Meth$^R$)(lac$^-$), *S. aureus* 76 (Meth$^R$)(lac$^+$), *S. aureus* ColBA (Meth$^S$)(lac$^-$), *E. faecium* ATCC 35667, or *E. faecalis* ATCC 29212.

The compositions containing the compound(s) of the invention can be administered for prophylactic and/or therapeutic treatments. In therapeutic applications, the compositions are administered to a patient already suffering from an infection, as described above, in an amount sufficient to cure or at least partially arrest the symptoms of the infection. An amount adequate to accomplish this is defined as "therapeutically effective amount or dose." Amounts effective for this use will depend on the severity and course of the infection, previous therapy, the patient's health status and response to the drugs, and the judgment of the treating physician. In prophylactic applications, compositions containing the compounds of the invention are administered to a patient susceptible to or otherwise at risk of a particular infection. Such an amount is defined to be a "prophylactically effective amount or dose." In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the compound of the invention will be in the range of 0.1 to 1000 milligram (mg) per recipient per day, preferably in the range of 1 to 100 mg per day. The desired dosage is preferably presented in one, two, three, four or more subdoses administered at appropriate intervals throughout the day. These subdoses can be administered as unit dosage forms, for example, containing 5 to 1000 mg, preferably 10 to 100 mg of active ingredient per unit dosage form. Preferably, the compounds of the invention will be administered in amounts of between about 2.0 mg/kg to 250 mg/kg of patient body weight, between about one to four times per day.

While it is possible to administer the active ingredient of this invention alone, it is preferable to present it as part of a pharmaceutical formulation. The formulations of the present invention comprise at least one compound or inhibitor of this invention in a therapeutically or pharmaceutically effective dose together with one or more pharmaceutically or therapeutically acceptable carriers. Solid carriers inlcude, e.g., starch, lactose, dicalcium phosphate, microcrystalline cellulose, sucrose, and kaolin, and optionally other therapeutic ingredients. Liquid carriers include, e.g., sterile water, polyethylene glycols, non-ionic surfactants, and edible oils such as corn, peanut and sesame oils. In addition, various adjuvants such as are commonly used in the art may be included. For example: flavoring agents, coloring agents, preservatives, and antioxidants, e.g., vitamin E, ascorbic acid, BHT and BHA. Various other considerations are described, e.g., in Gilman et al. (eds) (1990) Goodman and Gilman's: The Pharmacological Basis of Therapeutics, 8th Ed., Pergamon Press; and Remington's supra. Methods for administration are discussed therein, e.g., for oral, intravenous, intraperitoneal, or intramuscular administration, and others. Pharmaceutically acceptable carriers will include water, saline, buffers, and other compounds described, e.g., in the MERCK INDEX, Merck & Co., Rahway, N.J. Generally, preferred routes of administration are intravenous and intraperitoneal.

These pharmacological agents can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. Generally, a pharmacologically acceptable salt of the compound will be used to simplify preparation of the composition. Preferred salts include sodium, potassium, arginine, glycine, alanine, threonine. These are prepared, preferably, in water suitably mixed with a surfactant such as hydroxypropylcellulose.

Depending on the specific conditions being treated, such agents may be formulated and administered systemically or locally. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular subcutaneous, intramedullary injections, as well an intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art.

In soft capsules, the active compounds may be dissolved or suspended in suitable liquids, such as fatty oils, liquid paraffin, or liquid polyethylene glycols. In addition, stabilizers may be added.

EXAMPLES

The present invention will be more fully described in conjunction with the following specific examples which are not to be construed in any way as limiting the scope of the invention.

Example 1

In Vitro Antibacterial Evaluation

The compounds of the invention can be evaluated against several β-lactam resistant bacteria strains by determining the minimum inhibitory concentration (MIC, µg/ml) of each compound with respect to each strain. The MIC, the lowest concentration of antibiotic which inhibits growth of the test organism, is determined by the agar dilution method.

To determine the MIC for bacterial isolates, the test compound is incorporated in a series of two-fold dilutions into liquified Mueller-Hinton agar. Upon solidification, a number of different bacterial strains are spot inoculated with a replicating device onto the agar surface. After overnight incubation, the MIC breakpoint is determined as the lowest drug concentration that completely inhibited growth, disregarding a single colony or a faint haze. The procedures used in these stuides have been standardized by the National Committee for Clinical Laboratory Standards (NCCLS), as per the NCCLS publication entitled METHODS FOR DILUTION ANTIMICROBIAL SUSCEPTIBILITY TESTS (1991), which is incorporated herein by reference.

Aliquots of antimicrobial agents are prepared in phosphate buffered saline (PBS) at pH 7.2. Tween 20 or DMSO is used as a solubilizing vehicle as needed. Standard methods of vortexing, sonicating and gentle heat are used to facilitate solubilizing the test agent. Typically, the concentration of the stock solution is 10×that of the highest drug concentration tested. A 1.28 mg/mL stock solution is used with a subsequent highest working concentration of 128 µg/mL. Serial two-fold dilutions are done through ≦0.25 µg/mL. Each drug level is tested in duplicate. Two-fold drug dilutions are done in sterile 50 mL tubes with a final drug volume of 5 mL. Upon the addition of 45 mL of molten agar, a 10-fold dilution results. Two, 25 mL. plates are then poured into 15×150 mm square Petri plates with grids and allowed to harden.

A control plate with a reference drug, either cefotaxime, vancomycin or imipenem, is used as the positive growth control. Stock concentrations of reference antibiotics are prepared and frozen at −80° C. Upon preparation, the control plates are sealed and stored in the refrigerator for up to 1 week prior to use; however, imipenem control plates have to be prepared just prior to use. All test plates are used within 24 hours of preparation.

Satisfactory results are obtained where the inoculum contained about $10^4$ colony forming units (cfu)±0.5 logs. Starting with pure cultures of the test isolates on agar plates, a few isolated colonies are transferred to a tube of nutrient broth and allowed to grow 4–6 hours at 35–36° C. to reach log-phase growth. Dropwise addition of the broth culture to PBS is done to match a 0.5 McFarland turbidity standard equal to $10^8$ cfu/mL. This is further diluted ten-fold in PBS to reach a working inoculum concentration of $10^7$ cfu/mL. When 1 µL of the working inoculum is applied to the agar surface a concentration of about $10^4$ cfu per spot is obtained.

Disposable sterile 1 µL loops are used to inoculate test plates, with each isolate in a designated grid on the agar plate. An alternate method of inoculation involves the use of a replica plater, a device with 48 steel pins allowing the simultaneous inoculation of multiple isolates. After the spots have dried, the plates are incubated at 35°–36 C. for 16–20 hours. Endpoints are assessed as the minimum inhibitory concentration (MIC) of antimicrobial agent.

Example 2

In Vivo Antibacterial Evaluation

Compounds with superior activity in vitro when compared to reference antibiotics, are further evaluated in a murine model for lethal bacteremic peritonitis.

Groups of 5 female Swiss-Webster mice (Simonsen, Gilroy, Calif.) each are challenged by the intraperitoneal (IP) route with tenfold increments of a bacterial inoculum. This permits calculation of the mean lethal dose ($LD_{50}$) and the $LD_{100}$. For preliminary evaluation of a new antibiotic, mice are challenged IP with an $LD_{100}$ titer of bacteria. In two equal doses administered at the time of bacterial challenge and 2 hours later, groups of 10 mice each are treated subcutaneously with two-fold increments of the test drug and an antibiotic of known efficacy in mice and humans (i.e., positive control). Mice are observed for 72 h. Those alive at 72 h are considered long term survivors. The total drug dose in mg/kg that protects 50% of mice in a group from death is termed the mean protective dose ($PD_{50}$). $PD_{50}$s are similarly determined for several pathogens. The quantitative endpoints for the new drug are then compared with those obtained with reference antibiotics.

Six ten-fold dilutions of inoculum suspended in 0.5 mL of sterilized 7% hog gastric mucin (Sigma) are injected IP in groups of 5 mice each. A control group of 5 mice receive mucin alone. Mice are observed for 72 h. Those alive at 72 h are considered long term survivors. The mean lethal dose ($LD_{50}$) and 100% lethal dose ($LD_{100}$) are determined by the probit test.

For antibiotic efficacy studies, mice are challenged IP with bacterial titers that will afford an $LD_{100}$ for the test strain. In two equal doses administered at the time of bacterial challenge and 2 hours later, groups of 10 mice each are treated by the subcutaneous route (SC) with twofold increments of the test antibiotic; another group is treated similarly with a reference antibiotic of known efficacy in animals and man. Drug doses can range from 0.01 to 512 mg/kg. If the drug is poorly soluble, Tween 20 or propylene glycol will be employed to solubilize the drug. Animals are observed for 72 h. The 50% protective dose ($PD_{50}$) is calculated in mg/kg by the probit method. The $PD_{50}$ is the same as the 50% effective dose ($ED_{50}$) and the 50% curative dose ($CD_{50}$). Samples of blood from the hearts of all animals that die and from half the mice that survive are cultured on brain-heart infusion agar. Animals that received a protective dosage of the test drug will be alive at 72 h, although they may appear moderately ill to very ill during the observation period. Infected, placebo-treated control mice and those receiving non-effective i.e. lower dosages of the test drug will demonstrate a high rate of mortality. Most of these mice will die within 6 to 48 h. Those alive at 72 h will be considered long term survivors.

Thus, it will be appreciated that the compounds, methods and compositions of the invention are effective against various β-lactam resistant strains of bacteria which pose an increasing health risk to society.

Although certain embodiments and examples have been used to describe the present invention, it will be apparent to those skilled in the art that changes to the embodiments and examples shown may be made without departing from the scope or spirit of the invention.

Those references not previously incorporated herein by reference, including both patent and non-patent references, are expressly incorporated herein by reference for all purposes.

Other embodiments are within the following claims.

What is claimed:

1. A compound active against methicillin resistant bacteria, as demonstrated by a lower minimum inhibitory concentration against methicillin resistant strains than cefotaxime, of the formula:

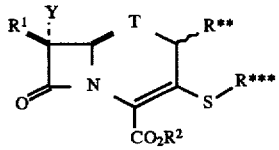

or a pharmaceutically acceptable salt thereof, wherein
T is selected from the group consisting of $CH_2$ and O;
Y is selected from the group consisting of H, OMe, and NHCHO;
R** is selected from the group consisting of H, Me, or Et;
$R^1$ is selected from the group consisting of —NHC(O) $ZR^3$; —$NR^4R^5$, and

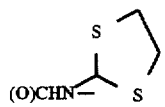

where Z is selected from the group consisting of —$CH_2(X^*)_m$—, —$C(NOR^6)$—, —CH ($OR^7$)—, —$C(CHCO_2R^8)$— and —$CH(NR^9R^{10})$—,
X* is selected from the group consisting of O and S, m is 0 or 1;
$R^3$ is selected from the group consisting of cyano, alkyl, aryl, heterocycle and heteroaralkyl wherein the heterocycle and the heteroaromatic portion of said heteroaralkyl are independently selected from the group consisting of optionally substituted furyl, thienyl, imidazolyl, indolyl, pyridinyl, thiadiazolyl, thiazolyl, piperazinyl, dibenzfuranyl, and dibenzthienyl;
$R^{4-7}$ are independently selected from the group consisting of hydrogen, alkyl, aryl and acyl;
$R^8$ is selected from the group of hydrogen, alkyl and aryl;
$R^9$ and $R^{10}$ are selected independently from the group consisting of hydrogen, alkyl, acyl, and heterocyclecarbonyl wherein the heterocyclic portion of said heterocyclecarbonyl is selected from the group consisting of optionally substituted furyl, thienyl, imidazolyl, indolyl, pyridinyl, thiadiazolyl, thiazolyl, piperazinyl, dibenzfuranyl, and dibenzthienyl;
$R^2$ is selected from the group consisting of hydrogen, alkyl, alkenyl, aryl, heterocycle, aralkyl, heteroaralkyl, and trialkylsilyl wherein the heterocycle and the heteroaromatic portion of said heteroaralkyl are independently selected from the group consisting of optionally substituted furyl, thienyl, imidazolyl, indolyl, pyridinyl, thiadiazolyl, thiazolyl, piperazinyl, dibenzfuranyl, and dibenzthienyl;
R*** is selected from the group consisting of heterotricycle;

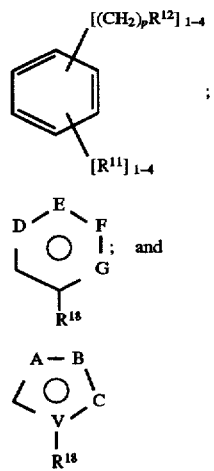

wherein
$R^{11}$ is H or halogen;
$R^{12}$ is

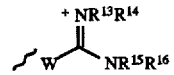

or S—$R^{17}$
W is selected from the group consisting of S, NH, and $CH_2$;
$R^{13-16}$ are independently selected from the group consisting of H, alkyl, cycloalkyl, acyl, hydroxy, amino, amidino, and phosphoryl and taken together may form a 5-or 6-membered ring;
$R^{17}$ is selected from the group consisting of alkyl, cycloalkyl, and a 5- or 6-membered ring heterocycle containing 0–4 nitrogen atoms, 0–1 oxygen atoms, and 0–1 sulfur atoms, and which is optionally substituted by alkyl, hydroxyl, alkoxyl, amino, hydroxymethyl, aminomethyl, or mono- or dialkylaminomethyl;

p is 0, 1 or 2;

$R^{18}$ is cyano or an optionally substituted phenyl or heteroaryl; wherein said heteroaryl is selected from the group consisting of optionally substituted furyl, thienyl, imidazolyl, indolyl, pyridinyl, thiadiazolyl, thiazolyl, piperazinyl, dibenzfuranyl, and dibenzthienyl V is carbon or nitrogen;

A, B and C are independently selected from the group consisting of $CR^{19}$ or nitrogen, where $R^{19}$ is hydrogen, alkyl, hydroxyl, amino, cyano, hydroxymethyl, or mono- or dialkylaminomethyl; and D, E, F, and G are independently selected from the group consisting of $CR^{19}$ or nitrogen, where $R^{19}$ is selected from the group consisting of hydrogen, alkyl, hydroxyl, amino, cyano, hydroxymethyl, and mono- or dialkylaminomethyl.

2. The compound of claim 1, wherein $R^1$ is —NHC(O)$ZR^3$.

3. The compound of claim 1, wherein $R^1$ is

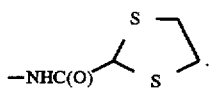

4. The compound of claim 2, wherein $R^3$ is alkyl, cyano, aryl or heterocycle.

5. The compound of claim 2, wherein $R^3$ is selected from the group consisting of methyl, cyano, phenyl, thienyl, furanyl, and 2-aminothiazolyl.

6. The compound of claim 2 wherein Z is —CH$_2$(X)$_m$—, X is S, and m is 0 or 1.

7. The compound of claim 6 wherein m is 1 and $R^3$ is alkyl substituted with a substitutent selected from the group consisting of guanidino, isothioureido and amidino.

8. The compound of claim 6, wherein Z is —C(NOR$^6$)—, $R^6$ is selected from the group consisting of hydrogen and alkyl, and $R^3$ is aryl or heterocycle.

9. The compound of claim 8, wherein $R^6$ is selected from the group consisting of 2-fluoroethyl, cyclopropylmethyl, allyl, dichloroallyl and cyclopentyl, and $R^3$ is selected from the group consisting of phenyl, 2-thienyl, 2-furyl and 2-aminothiazol-4-yl.

10. The compound of claim 1, wherein p is 1, and $R^{12}$ is

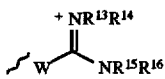

where W=S or NH, and $R^{13}$-$R^{16}$ are hydrogen.

11. The compound of claim 1 wherein said compound is a 7-acylamido-3-(arylthio) carbacephem.

12. The compound of claim 1 wherein said compound is a 7-acylamido-3-(arylthio) oxacephem.

13. The compound of claim 1 wherein said compound is a 7-acylamido-7α-methoxy-3-(arylthio)cephem.

14. The compound of claim 1 wherein said compound is a 7-acylamido-7α-methoxy-3-(arylthio)carbacephem.

15. The compound of claim 1 wherein said compound is a 7-acylamido-7α-methoxy-3-(arylthio)oxacephem.

16. The compound of claim 1 wherein said compound is a 7-acylamido-7α-formamido-3-(arylthio)cephem.

17. The compound of claim 1 wherein said compound is a 7-acylamido-7α-formamido-3-(arylthio)carbacephem.

18. The compound of claim 1 wherein said compound is a 7-acylamido-7α-formamido-3-(arylthio)oxacephem.

19. A method of treating a mammal suffering from a methicillin resistant or methicillin sensitive bacterial infection, comprising administering to such mammal a therapeutically effective amount of a compound of claim 1 to thereby at least partially relieve said mammal from said methicillin resistant or methicillin sensitive bacterial infection.

20. The method of claim 19, wherein said mammal is infected with a methicillin resistant or methicillin sensitive Staphylococcal or Entererococcal organism.

21. An antibacterial composition for treating a methicillin resistant or methicillin sensitive bacterial infection, comprising a therapeutically effective amount of a compound of claim 1 in a pharmaceutically acceptable carrier.

22. The composition of claim 21, wherein said bacteria is a methicillin resistant or methicillin sensitive Staphylococcal or Enterococcal organism.

* * * * *